United States Patent [19]

Hertz et al.

[11] 4,132,779

[45] Jan. 2, 1979

[54] ANTIBIOTIC BL580 ZETA AND USE THEREOF AS ANTICOCCIDIAL AGENT

[75] Inventors: Martin R. Hertz, Pearl River; John H. E. J. Martin, New City, both of N.Y.

[73] Assignee: American Cyanamid Company, Stamford, Conn.

[21] Appl. No.: 807,867

[22] Filed: Jun. 20, 1977

[51] Int. Cl.² ............................................. A61K 35/00
[52] U.S. Cl. ................................... 424/122; 195/80 R
[58] Field of Search ....................... 424/122; 195/80 R

[56] References Cited

U.S. PATENT DOCUMENTS

| 3,595,955 | 7/1971 | Boer et al. | 424/122 |
| 3,711,605 | 1/1973 | Hamill et al. | 424/122 |
| 3,993,749 | 11/1976 | Sehgal et al. | 424/122 |

*Primary Examiner*—Jerome D. Goldberg
*Attorney, Agent, or Firm*—Edward A. Conroy, Jr.

[57] ABSTRACT

This disclosure describes a new antibiotic designated BL580 ZETA produced in a microbiological fermentation under controlled conditions using a new strain of *Streptomyces hygroscopicus* and mutants thereof. This new antibiotic is an active anticoccidial agent.

7 Claims, 4 Drawing Figures

$^{13}C$ NUCLEAR MAGNETIC RESONANCE SPECTRUM OF BL580 ZETA SODIUM SALT IN $CDCl_3$

PROTON MAGNETIC RESONANCE SPECTRUM OF BL580 ZETA SODIUM SALT IN CDCl_3

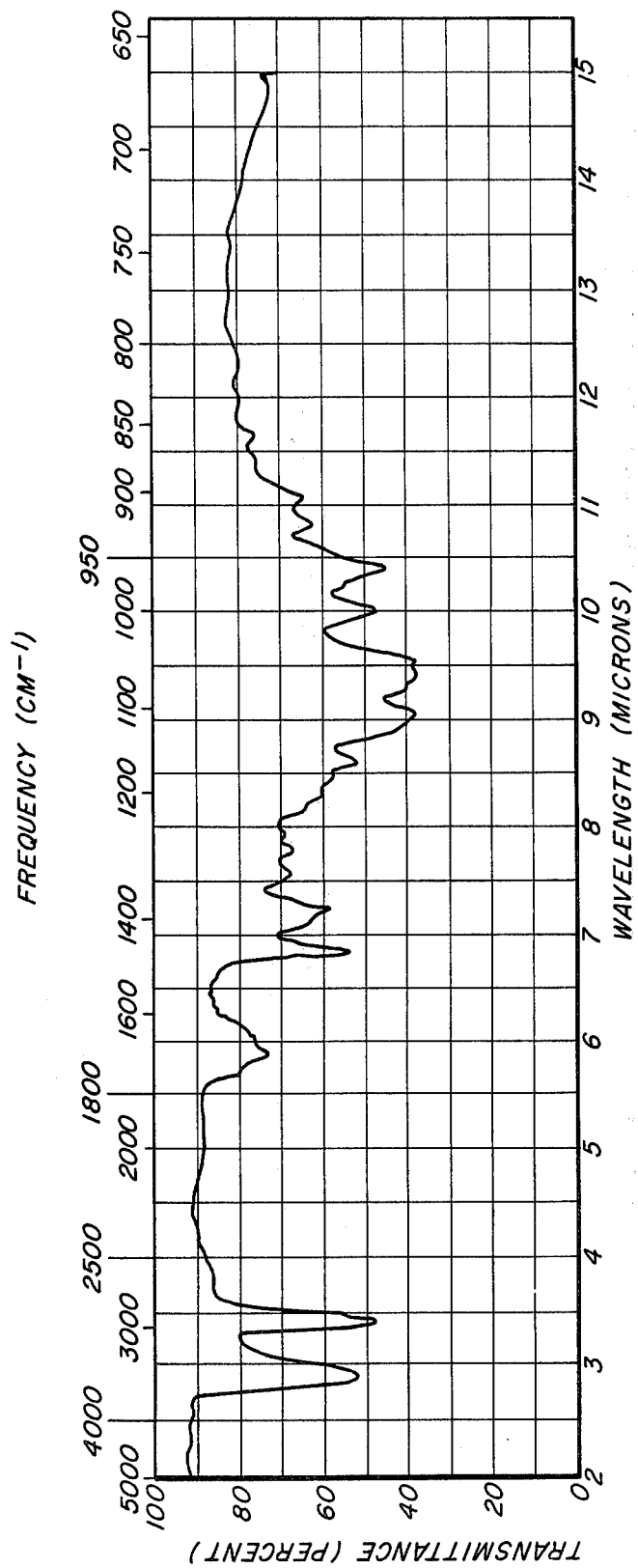

ANTIBIOTIC BL580 ZETA AND USE THEREOF AS ANTICOCCIDIAL AGENT

BRIEF SUMMARY OF THE INVENTION

This invention relates to a new antibiotic designated BL580 ZETA, to its production by fermentation, to methods for its recovery and concentration from crude solutions, and to processes for its purification. The present invention includes within its scope the antibiotic BL580 ZETA in dilute form, as a crude concentrate, and in its pure crystalline form. The effects of this new antibiotic as an anticoccidial agent together with its chemical and physical properties differentiate it from previously described antibiotics.

DETAILED DESCRIPTION OF THE INVENTION

Figure 1:
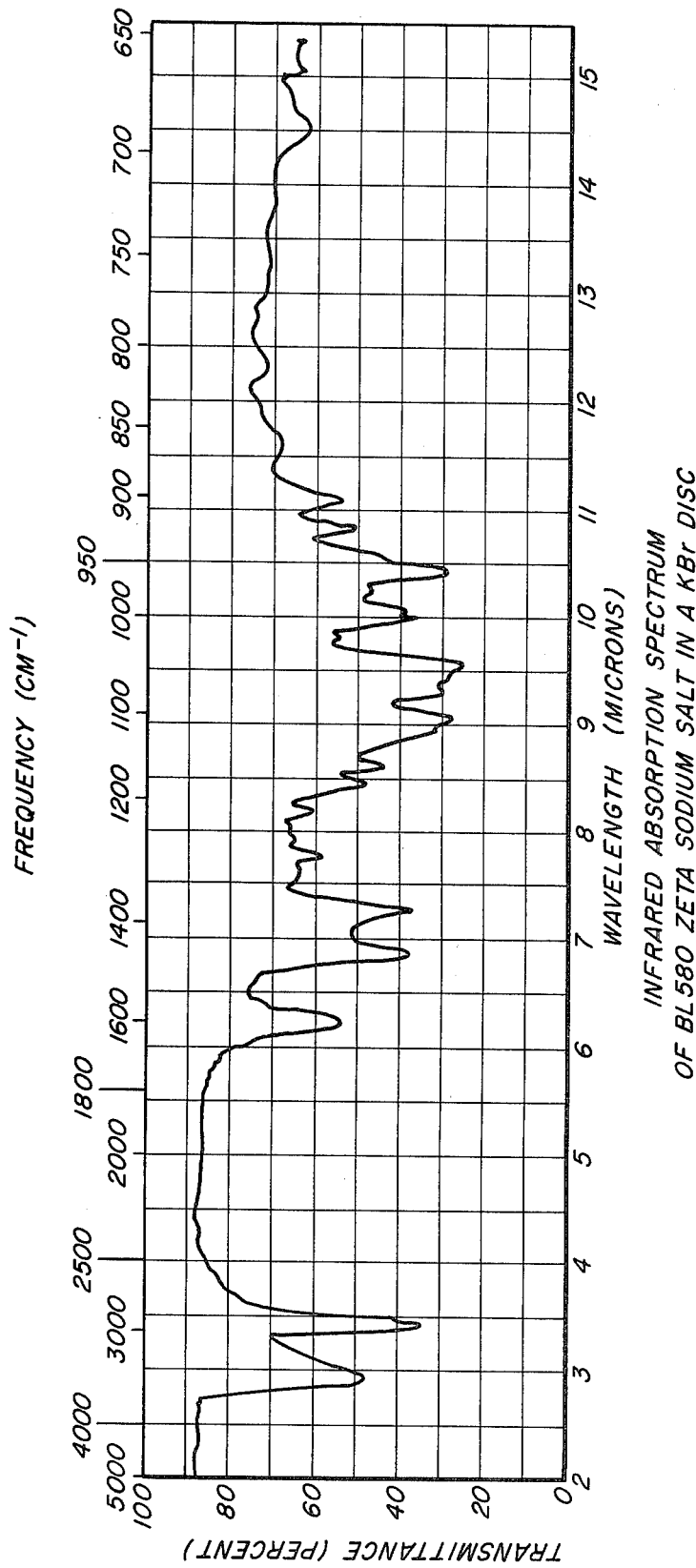

The novel antibiotic of the present invention is an organic acid and thus is capable of forming salts with alkali metal ions. Thus, salts formed by admixture of the antibiotic free acid with stoichiometric amounts of alkali metal ions, suitably in a neutral solvent, are formed with ions such as sodium ion, potassium ion, ammonium ion, and related cations. The alkali metal ion salts of BL580 ZETA are, in general, crystalline solids, relatively insoluble in water but soluble in most common organic solvents such as methanol, ethyl acetate, acetone, chloroform, heptane, ether, and benzene.

The new antibiotic, which has been designated BL580 ZETA, is formed during the cultivation under controlled conditions of a new mutant strain of *Streptomyces hygroscopicus* which is derived by treatment of a natural selection, single colony isolate of *S. hygroscopicus* NRRL 5647 with N-methyl-N'-nitro-N"-nitrosoguanidine. A viable culture of the new mutant strain has been deposited with the Culture Collection Laboratory, Northern Regional Research Center, United States Department of Agriculture, Peoria, Illinois and has been added to its permanent collection under its accession number NRRL 11108.

The cultural, physiological, and morphological features of NRRL 11108 are substantially the same as those of NRRL 5647 (as determined by Dr. H. D. Tresner, Lederle Laboratories Division, American Cyanamid Company, Pearl River, New York) except that NRRL 11108 produces little or no sporulation on most media. A general description of NRRL 5647 is published in U.S. Pat. No. 3,812,249.

It is to be understood that for the production of BL580 ZETA, the present invention is not limited to this particular microorganism or to microorganisms fully answering the growth and microscopic characteristics of NRRL 11108. In fact, it is desired and intended to include the use of mutants produced from NRRL 11108 by various means, such as X-radiation, ultraviolet radiation, nitrogen mustard, phage exposure and the like.

Antibiotic BL580 ZETA is an active anticoccidial agent as evidenced by the following in vivo tests wherein the following poultry diet is used:

| | |
|---|---|
| Vitamin-Amino Acid Premix | 0.5% |
| Trace Minerals | 0.1% |
| Sodium Chloride | 0.3% |
| Dicalcium Phosphate | 1.2% |
| Ground Limestone | 0.5% |
| Stabilized Fat | 4.0% |
| Dehydrated Alfalfa (17% protein) | 2.0% |
| Corn Gluten Meal (41% protein) | 5.0% |
| Menhaden Fish Meal (60% protein) | 5.0% |
| Soybean Oil Mean (44% protein) | 30.0% |
| Ground Yellow Corn, fine to | 100% |

The vitamin-amino acid premix in the above poultry diet was prepared from the following formulation. The expressions of quantity relate to units per kilogram of the poultry diet.

| | | |
|---|---|---|
| Butylated Hydroxy Toluene | 125 | mg. |
| dl-Methionine | 500 | mg. |
| Vitamin A | 3300 | I.U. |
| Vitamin $D_3$ | 1100 | I.C.U. |
| Riboflavin | 4.4 | mg. |
| Vitamin E | 2.2 | I.U. |
| Niacin | 27.5 | mg. |
| Pantothenic Acid | 8.8 | mg. |
| Choline Chloride | 500 | mg. |
| Folic Acid | 1.43 | mg. |
| Menadione Sodium Bisulfate | 1.1 | mg. |
| Vitamin $B_{12}$ | 11 | mcg. |
| Ground Yellow Corn, fine to | 5 | gm. |

A mixed inoculum of 5000 sporulated oocysts of *Eimeria acervulina* and a sufficient number of oocysts of *Eimeria tenella* to produce 85% to 100% mortality in untreated controls was given to groups of seven-day-old chicks, by direct inoculation into the crops of all chicks. The chicks were given free access to the poultry diet and water during the entire test period. Two days after inoculation, medicated feed, composed of the poultry diet and several levels of BL580 ZETA, was presented to the various groups of chicks in the test. Ten days after inoculation the tests were terminated. The chicks were weighed, necropsied and their intestinal tracts examined for lesions. The results of this test appear in Table I below. These results show that 80% survival of infected chicks was obtained when 60 ppm of BL580 ZETA was administered to infected chicks in their diet. These results also show a significant suppression of lesions due to *Eimeria tenella* and *Eimeria acervulina* when 30 ppm or 60 ppm of BL580 ZETA is administered to infected chicks in their diet.

TABLE I

| Concentration of BL580 ZETA in Diet ppm. | Number of Birds Started | Percent Survival | Percent Birds with Reduced Lesions | |
|---|---|---|---|---|
| | | | *Eimeria tenella* | *Eimeria acervulina* |
| 0 | 40 | 15 | 0 | 0 |
| 60 | 10 | 80 | 80 | 90 |
| 30 | 10 | 50 | 10 | 50 |

Cultivation of the microorganism *Streptomyces hygroscopicus* NRRL 11108 may be carried out in a wide variety of liquid culture media. Media which are useful for the production of antibiotic BL580 ZETA include an assimiable source of carbon such as starch, sugar, molasses, glycerol, etc.; an assimilable source of nitrogen such as protein, protein hydrolysate, polypeptides, amino acids, corn steep liquor, etc.; and inorganic anions and cations such as potassium, sodium, calcium, sulfate, phosphate, chloride, etc. Trace elements such as boron, molybdenum, copper, etc. are supplied as impurities of other constituents of the media. Aeration in tanks and bottles is provided by forcing sterile air through or onto the surface of the fermenting medium. Further agitation in tanks is provided by a mechanical impeller. An antifoaming agent such as one percent octadecanol in lard oil may be added as needed.

Shaker flask inoculum of *Streptomyces hygroscopicus* NRRL 11108 is prepared by inoculating 100 ml. portions of sterile liquid medium in 500 ml. flasks with scrapings or washings of spores from an agar slant of the culture. The following medium is ordinarily used:

| Soy flour | 1.0% |
|---|---|
| Glucose | 2.0% |
| Corn steep liquor | 0.5% |
| $CaCO_3$ | 0.3% |
| Water q.s.ad. | 100% |

The flasks are incubated at a temperature from 25° C. to 29° C., preferably 28° C. and agitated vigorously on a rotary shaker for 48 to 96 hours. Two 100 ml. portions of this inoculum are used to inoculate 12 liters of the same sterile medium in a 20 liter bottle. This inoculum is incubated with agitation and aeration of sterile air for 36 to 64 hours at 25° C. to 29° C., preferably 28° C. This inoculum is used to inoculate 300 liters of the same sterile medium in a tank fermentor. This inoculum is incubated with agitation and aeration of sterile air for 36 to 64 hours at 25° C. to 29° C., preferably 28° C. This inoculum is used to inoculate a 4000 liter fermentation tank containing 3000 liters of a sterile medium such as the following:

| Corn steep liquor | 0.5% |
|---|---|
| Soy Flour | 1.0% |
| Corn starch | 4.0% |
| $CaCO_3$ | 0.1% |
| Water q.s.ad. | 100% |

This medium is fermented for 100 to 200 hours at a temperature of 27° C. to 32° C. with agitation by an impeller and aeration at a rate of 0.4–0.8 liters of air per liter of medium per minute. Normally a defoamer such as Hodag ® FD82 is added at a ratio of about 3.5 gal./1000 gal. of medium.

After the fermentation is completed, the fermented mash containing antibiotic BL580 ZETA is combined with about one-half its volume of ethyl acetate and stirred for 2-3 hours. An approximate 8% portion of diatomaceous earth is added and the mixture is filtered through a plate and frame filter press. The cake is washed on the press with ethyl acetate. The ethyl acetate extracts are collected and concentrated in a still to a syrup. The syrup is stirred with twice its volume of n-heptane and stored at 4° C. overnight. The supernatant is recovered by decantation and concentrated to a gummy concentrate which is treated with 10 liters of methanol and chilled with the aid of dry ice for several hours. The mixture is filtered through sintered glass with a diatomaceous earth precoat and washed with cold methanol. The methanol solution is concentrated to a syrupy residue in vacuo.

A chromatographic column is prepared with activated carbon at a ratio of about one liter of carbon per 50 grams of charge. The dried residue is dissolved in methylene chloride at a ratio of 40 grams/liter and charged on the column. The methylene chloride eluate is collected as one cut and concentrated to a syrup. The residue is mixed with methanol and stored in a chill room with dry ice to reduce the temperature to −10° C. for 15 minutes. After 15 minutes the solidified oil is filtered off and the methanol soluble material is concentrated in vacuo giving an oil. This oil is dissolved in a minimum amount of methylene chloride, combined with silica gel, concentrated until no more solvent is present, and charged on a dry silica gel column. The column is developed with 1:1 ethyl acetate:benzene. The column is then allowed to drain. The section of column comprising Rf 0.10 to 0.45 is excised from the column and slurried in ethyl acetate:methylene chloride:methanol (2:2:1 by volume). This mixture is filtered, washed with additional solvent mixture and concentrated in vacuo to dryness.

A two phase system is prepared by mixing n-heptane:methanol:ethyl acetate:water (3000:1500:20:40 by volume). Celatom ® (Eagle-Picher Industries, Cincinnati, Ohio), a brand of diatomaceous earth, is mixed with the lower phase of this system at a ratio of about 2000 grams/1650 ml. of lower phase and packed in increments into a (7.5 cm. inside diameter) column. The charge is applied as a mixture of diatomaceous earth, lower phase, and lyophillized product. The charged column is developed with upper phase and fractions are collected. The activity is detected by thin layer chromatography on selected fractions using a gelplate, chloroform:ethyl acetate (1:1) as developer, and charred with $H_2SO_4$ for detection. Fractions 123-186 (end) are combined and concentrated giving antibiotic BL580 ZETA.

The invention will be described in greater detail in conjunction with the following specific examples.

EXAMPLE 1

Inoculum Preparation

A typical medium used to grow the primary inoculum is prepared according to the following formula:

| Soy flour | 1.0 gm. |
|---|---|
| Glucose | 2.0 gm. |
| Corn steep liquor | 0.5 gm. |
| $CaCO_3$ | 0.3 gm. |
| Water to | 100 ml. |

The washed or scraped spores from an agar slant of *Streptomyces hygroscopicus* NRRL 11108 are used to inoculate two 500 ml. flasks each containing 100 ml. of the above medium which has been sterilized. The flasks are placed on a rotary shaker and agitated vigorously for 72 hours at 28° C. The resulting flask inoculum is transferred to a 5 gallon glass bottle containing 12 liters of the same sterile medium. This secondary inoculum is aerated with sterile air while growth is carried out for 48 hours at 28° C. The resulting secondary inoculum is transferred to a 100 gallon tank containing 300 liters of the same sterile medium. This tertiary inoculum is aerated with sterile air at the rate of one liter of air/liter of medium/minute and agitated by an impeller operating at 173 rpm. Growth is continued for 48 hours at 28° C. The pH at this time is 6.9 to 7.0.

EXAMPLE 2

Fermentation

A fermentation medium is prepared according to the following formula:

| | |
|---|---|
| Corn steep liquor | 0.5 gm. |
| Soy flour | 1.0 gm. |
| Corn starch | 4.0 gm. |
| CaCO$_3$ | 0.1 gm. |
| Water to | 100 ml. |

A 3000 liter batch of fermentation medium of the above formulation in a 4000 liter tank is sterilized at 120° C. for 60 minutes. The pH of the medium after sterilization is 6.4 to 6.5. This medium is inoculated with 300 liters of tertiary inoculum prepared as described in Example 1. The fermentation is carried out at 28°–29° C. using 11.0 liters of Hodag ® FD82 as a defoaming agent. Aeration is supplied at the rate of 0.6 liter of sterile air per liter of mash per minute. The mash is agitated by an impeller driven at 150 rpm. At the end of 138 hours of fermentation time the mash is harvested.

EXAMPLE 3

Isolation and Purification

A 2600 liter portion of fermented mash prepared as described in Example 2, having a pH of 7.3, is combined with 1300 liters of ethyl acetate and stirred for ½ hour. An 8% (by weight) portion of diatomaceous earth is added. The mixture is filtered in several portions, with stirring, through a pair of frame presses. The aqueous-ethyl acetate filtrates are pooled providing 3300 liters which is allowed to separate, providing 1100 liters of ethyl acetate extract. After each portion of mash-ethyl acetate-diatomaceous earth is filtered through a press, the pad is washed on the press with ethyl acetate. The ethyl acetate washings are combined and separated giving 600 liters of ethyl acetate washings. The 1100 liters of ethyl acetate extracts and 600 liters of ethyl acetate washings are combined and concentrated in a 400 gallon still to about 100 liters. This 100 liters is further concentrated in a 50 gallon still to 20 liters. This 20 liters is further concentrated in a glass still to a syrup.

The syrup is stored at 4° C. for 48 hours and then stirred with twice its volume of n-heptane. The mixture is allowed to stand at 4° C. overnight. The supernatant is recovered by decantation and concentrated to a gummy residue. A 10 liter portion of methanol is added to the gummy residue and the mixture is chilled with the aid of dry ice for several hours. The mixture is filtered through sintered glass containing a diatomaceous earth precoat and washed with cold methanol. The combined filtrate and washings are concentrated to a syrup in vacuo providing 1124 grams of residue. This residue is dissolved in methylene chloride at a rate of 33 grams/liter. A chromatographic column is prepared by packing with 27 liters of 20×40 mesh granular carbon. The residue in methylene chloride is passed through this column at a flow rate of 400 ml. per minute. The methylene chloride eluate is collected as one cut and concentrated to a syrup. The residue is thoroughly mixed with methanol. The mixture is reduced to −10° C. in a chill room with the aid of dry ice and maintained at −10° C. for 15 minutes. Any solidified oil is removed by filtration and the methanol filtrate is concentrated to a syrup in vacuo giving 363.8 grams as an oil.

A dry pack chromatographic column is prepared by packing 4 kg. of silica gel into a 12 inch circumference plastic column. A 200 gram portion of the above oil is dissolved in a minimal amount of methylene chloride. A 300 gram portion of silica gel is added and mixed thoroughly and the mixture is then concentrated in vacuo to dryness. The dried mixture is charged on the column and some sea sand is placed on the top of the column to prevent bed disturbance during elution. The plastic column is placed in a glass shell to give it support. The column is eluted with 9.4 liters of 1:1 ethyl acetate:benzene. Cuts are collected and the column is allowed to run dry. The section of column Rf 0.10 to Rf 0.45 is removed and slurried in ethyl acetate:methylene chloride:methanol (2:2:1). The mixture is filtered and washed with the same solvent mixture and concentrated to dryness in vacuo, giving 22 grams of residue.

A two-phase system is prepared by mixing n-heptane:methanol:ethyl acetate:water [3000:1500:20:40 (by volume)]. A 2000 gram portion of acid washed diatomaceous earth is mixed with 1650 ml. of the lower phase of this solvent system and packed in increments into a (7.5 cm. inside diameter) glass column. Twenty-two grams of residue are dissolved in lower phase, filtered and the filtrate is mixed with diatomaceous earth and charged on the column. The charged column is developed with the upper phase of the solvent system and cuts are collected via a fraction collector. The desired compound is located by assaying fraction samples with thin layer chromatography. Fractions 123-186 (end) are combined, concentrated to a residue in vacuo, dissolved in tert-butyl alcohol and lyophilized providing 4.2 gm. of the product BL580 ZETA.

EXAMPLE 4

Preparation of the Sodium Salt of BL580 ZETA

A 900 mg. portion of BL580 ZETA is dissolved in a mixture of 30 ml. of diethyl ether and 70 ml. of low boiling petroleum ether. This solution is stirred along with an equal volume of water. The mixture is adjusted to pH 2.0 with 1N HCl while stirring. The aqueous phase is discarded. Fresh water is added. The two phase system is stirred and the pH is adjusted to 10.0 using 0.1N NaOH. The resulting emulsion is centrifuged. The upper phase is concentrated in vacuo giving a white residue. This residue is dissolved in 15 ml. of diethyl ether and 30 ml. of low boiling petroleum ether. The solution is allowed to evaporate in a chill room at 4° C. for 18 hours reducing the volume by about 50%. The insoluble material is collected by filtration and washed with petroleum ether giving a white solid. The filtrate is evaporated and treated as above giving a second crop. This second filtrate is evaporated and treated as above giving a third crop. The first and third crops are combined giving 445 mg. of the sodium salt of BL580 ZETA.

Figure 2:
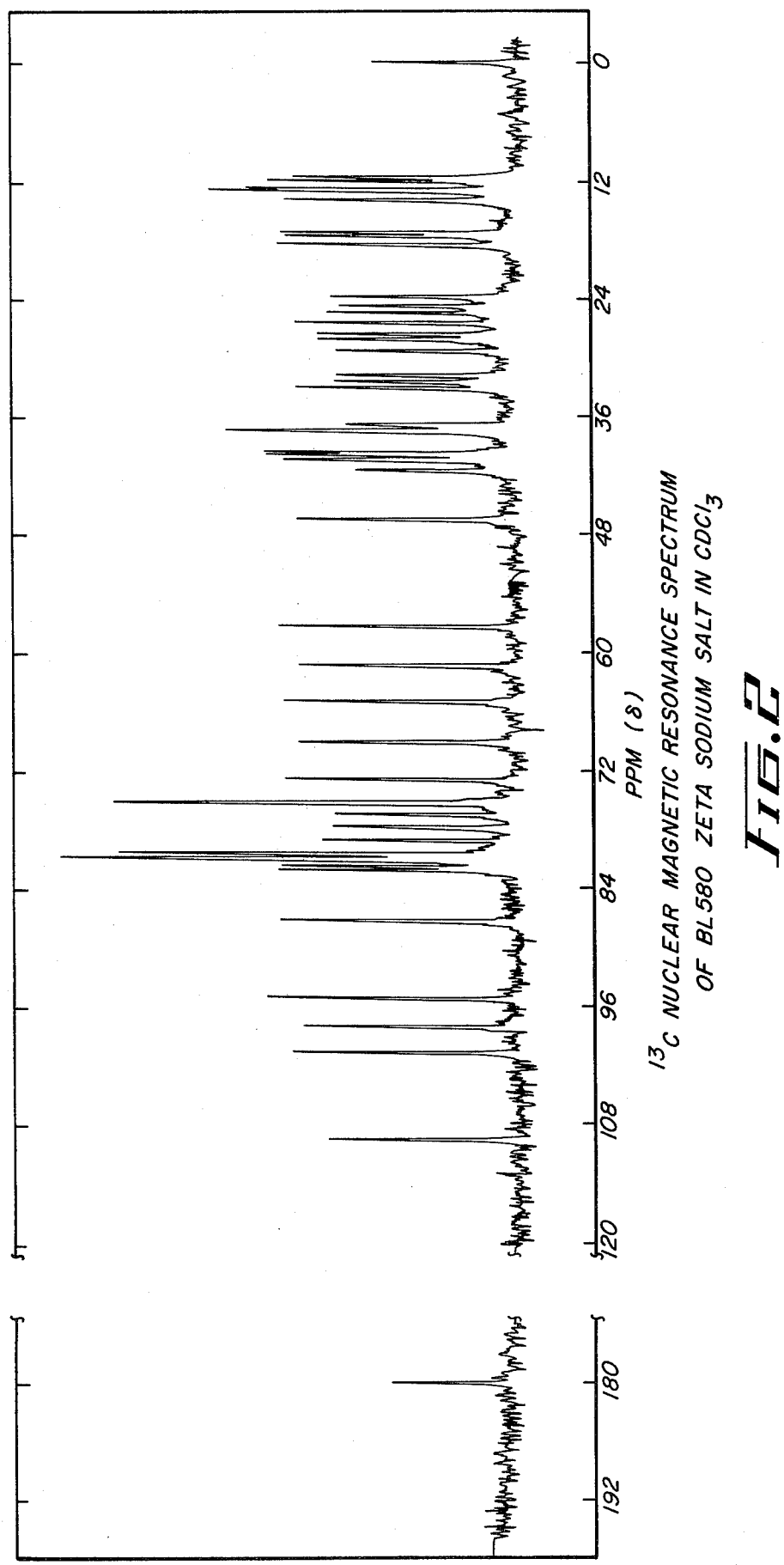
Figure 3:
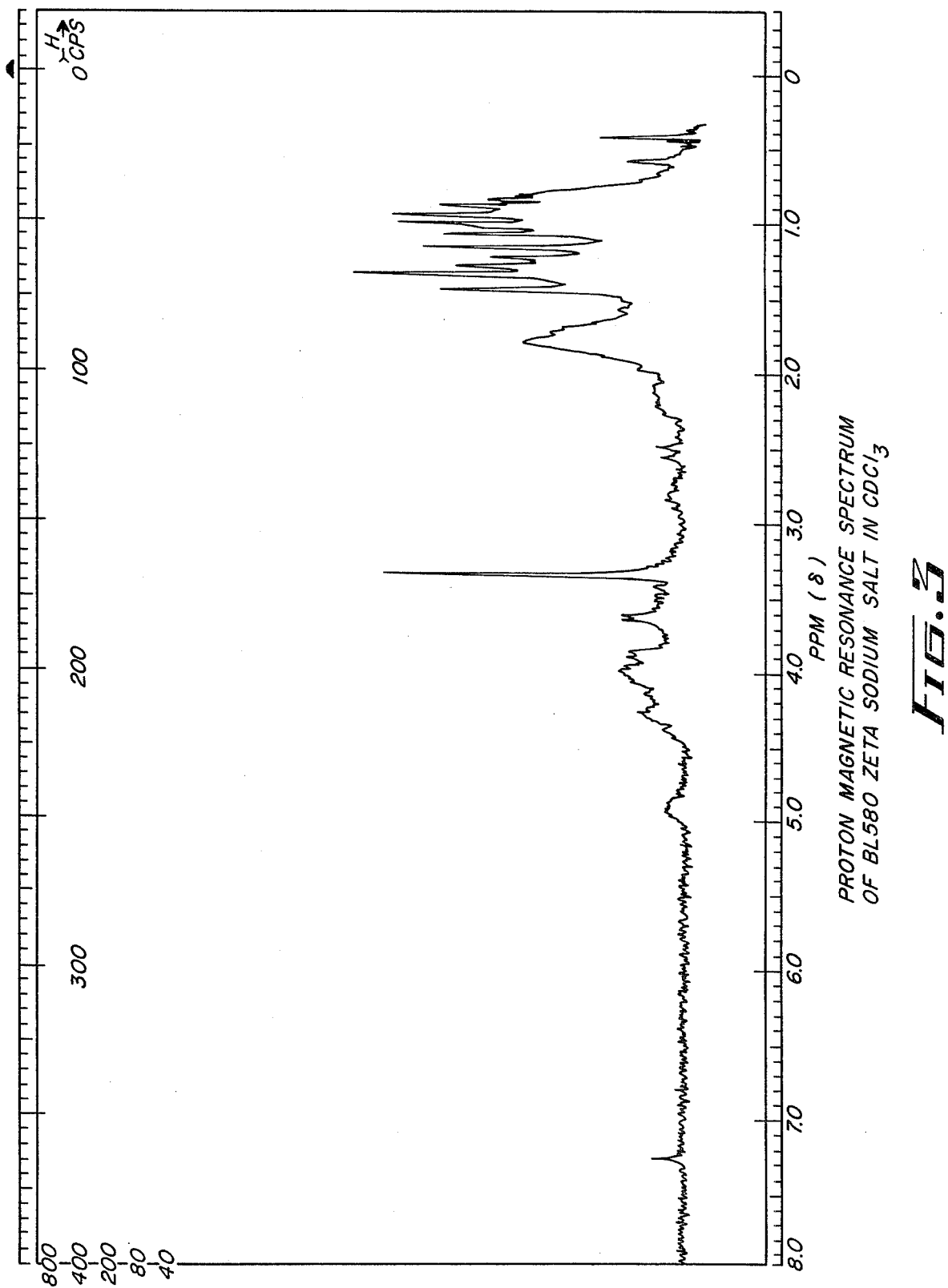

This sodium salt of BL580 ZETA has a melting point of 162° C.; a specific rotation $[\alpha]_D^{20} = -3°\pm2°$ (C=0.94 in methanol); and an elemental analysis (percent): C,60.97; H,8.69; Na,2.70. The sodium salt of BL580 ZETA exhibits characteristic absorption in the infrared region of the spectrum at the following wavelengths; 2.93 μ, 3.43 μ, 6.12 μ, 7.27 μ, 8.63 μ, 9.07 μ, 9.57 μ, 10.05 μ, and 10.45 μ. A standard infrared absorption spectrum of BL580 ZETA sodium salt is shown in FIG. 1 of the accompanying drawings. A standard $^{13}$C nuclear magnetic resonance spectrum of BL580 ZETA sodium salt is shown in FIG. 2 of the accompanying drawings. A standard proton magnetic resonance spectrum of BL580 ZETA sodium salt is shown in FIG. 3 of the accompanying drawings.

EXAMPLE 5

Preparation of the Free Acid of BL580 ZETA

A 125 mg. portion of the sodium salt of BL580 ZETA is dissolved in 100 ml. of diethyl ether. A 100 ml. portion of water is added and the pH is adjusted to 2.0 with 1N HCl while stirring. The ether layer is separated and washed with a fresh portion of water. The washed ether is concentrated in vacuo. The residue is dissolved in t-butanol and lyophilized giving 106 mg. of the free acid of BL580 ZETA.

This free acid of BL580 ZETA has a melting point of 105°–107° C.; a specific rotation $[\alpha]_D^{20} = 7° \pm 2°$ (C=0.9 in methanol); and an elemental analysis (percent): C,63.99; H,9.43. The free acid of BL580 ZETA exhibits characteristic absorption in the infrared region of the spectrum at the following wavelengths; 2.87 $\mu$, 3.40 $\mu$, 3.80 $\mu$, 5.87 $\mu$, 8.62 $\mu$, 9.02 $\mu$, 9.45 $\mu$, 9.57 $\mu$, 10.04 $\mu$, and 10.43 $\mu$. A standard infrared absorption spectrum of the free acid of BL580 ZETA is shown in FIG. 4 of the accompanying drawings.

We claim:

1. Antibiotic BL580 ZETA free acid, a compound which
   (a) is effective as an anticoccidial agent; and in its essentially pure crystalline form;
   (b) has a melting point of 105°–107° C.;
   (c) has the following elemental analysis (percent): C, 63.99; H, 9.43;
   (d) has an optical rotation $[\alpha]_D^{20} = 7° \pm 2°$ (C = 0.9 in methanol);
   (e) has a characteristic infrared absorption spectrum as shown in FIG. 4 of the drawings.

2. Antibiotic BL580 ZETA sodium salt, a compound which
   (a) is effective as an anticoccidial agent; and in its essentially pure crystalline form;
   (b) has a melting point of 162° C;
   (c) has the following elemental analysis (percent): C, 60.97; H, 8.69; Na, 2.70;
   (d) has an optical rotation $[\alpha]_D^{20} = -3° \pm 2°$ (C = 0.94 in methanol);
   (e) has a characteristic infrared absorption spectrum as shown in FIG. 1 of the drawings;
   (f) has a characteristic $^{13}C$ nuclear magnetic resonance spectrum as shown in FIG. 2 of the drawings;
   (g) has a characteristic proton magnetic resonance spectrum as shown in FIG. 3 of the drawings.

3. A process for the production of antibiotic BL580 ZETA which comprises cultivating *Streptomyces hydroscopicus* NRRL 11108 in an aqueous nutrient medium containing assimilable sources of carbohydrate, nitrogen, and inorganic salts under submerged aerobic conditions until substantial activity is imparted to said medium, and then recovering antibiotic BL580 ZETA as defined in claim 1 therefrom.

4. A method of treating and preventing coccidiosis in poultry which comprises administering orally to said poultry an anticoccidally-effective amount of antibiotic BL580 ZETA as defined in claim 1.

5. The method of claim 4 wherein the antibiotic is administered orally to poultry at a concentration in the diet of about 30 ppm and about 60 ppm.

6. A composition of matter for the treatment and prevention of coccidiosis in poultry which comprises a poultry diet and an anticoccidally-effective amount of antibiotic BL580 ZETA as defined in claim 1.

7. A composition according to claim 6 wherein the antibiotic is present in the diet at a concentration of about 30 ppm and about 60 ppm.

* * * * *